(12) United States Patent
Rao et al.

(10) Patent No.: US 11,264,135 B2
(45) Date of Patent: Mar. 1, 2022

(54) MACHINE-AIDED WORKFLOW IN ULTRASOUND IMAGING

(71) Applicant: Siemens Medical Solutions USA, Inc., Malvern, PA (US)

(72) Inventors: Bimba Rao, San Jose, CA (US); Ismayil M. Guracar, Redwood City, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 940 days.

(21) Appl. No.: 15/809,802

(22) Filed: Nov. 10, 2017

(65) Prior Publication Data

US 2019/0148011 A1 May 16, 2019

(51) Int. Cl.
*A61B 8/08* (2006.01)
*G16H 50/20* (2018.01)
*G06T 7/00* (2017.01)
*A61B 8/00* (2006.01)
*G16H 30/40* (2018.01)

(52) U.S. Cl.
CPC ........... *G16H 50/20* (2018.01); *A61B 8/5223* (2013.01); *A61B 8/5292* (2013.01); *A61B 8/54* (2013.01); *G06T 7/0012* (2013.01); *G16H 30/40* (2018.01); *A61B 8/461* (2013.01); *A61B 8/523* (2013.01); *A61B 8/5207* (2013.01)

(58) Field of Classification Search
CPC ...... G16H 50/20; G16H 30/40; G06T 7/0012; G06T 7/11; G06T 2207/20084; G06T 2207/30084; G06T 2207/10132; G06T 2207/10016; A61B 8/54; A61B 8/5223; A61B 8/5292; A61B 8/5207; A61B 8/523; A61B 8/461
See application file for complete search history.

(56) References Cited

U.S. PATENT DOCUMENTS

| | | | |
|---|---|---|---|
| 6,656,120 B2 | 12/2003 | Lee et al. | |
| 7,244,230 B2 | 7/2007 | Duggirala et al. | |
| 7,648,460 B2 | 1/2010 | Simopoulos et al. | |
| 7,680,312 B2 | 3/2010 | Jolly et al. | |

(Continued)

OTHER PUBLICATIONS

Baumgartner, Christian F., et al. "Real-Time Detection and Localisation of Fetal Standard Scan Planes in 2D Freehand Ultrasound." arXiv preprint arXiv:1612.05601 (2016).

(Continued)

*Primary Examiner* — Peter Luong

(57) ABSTRACT

Using computer-assisted classification and/or computer-assisted segmentation with or without monitoring the field of view for change, the workflow for ultrasound imaging may be made more efficient. The classification and/or segmentation is used to perform a next act in the sequence of acts making up the ultrasound examination. Rather than requiring a user to determine the act and implement the act, the ultrasound scanner determines and implements the act based on the identification and/or location of an imaged object. For example, the identification of the object as a kidney using a machine-learnt classifier triggers a color flow scan, and the location of the object determines a placement for the color flow region of interest (ROI), avoiding the user having to perform the ROI initiation and/or placement and increasing workflow efficiency.

20 Claims, 5 Drawing Sheets

(56) References Cited

U.S. PATENT DOCUMENTS

| | | |
|---|---|---|
| 7,747,054 B2 | 6/2010 | Zhou et al. |
| 7,804,999 B2 | 9/2010 | Zhou et al. |
| 7,876,934 B2 | 1/2011 | Georgescu et al. |
| 8,092,388 B2 | 1/2012 | Park et al. |
| 8,170,303 B2 | 5/2012 | Zhou et al. |
| 8,296,247 B2 | 10/2012 | Zhang et al. |
| 8,831,311 B2 | 9/2014 | Swamy et al. |
| 9,033,887 B2 | 5/2015 | Ionasec et al. |
| 9,183,226 B2 | 11/2015 | Yee et al. |
| 9,230,192 B2 | 1/2016 | Jin et al. |
| 9,324,022 B2 | 4/2016 | Williams, Jr. et al. |
| 9,342,758 B2 | 5/2016 | Xue |
| 9,569,736 B1 | 2/2017 | Ghesu et al. |
| 9,607,373 B2 | 3/2017 | Buisseret et al. |
| 9,760,690 B1 | 9/2017 | Petkov et al. |
| 2005/0010098 A1 | 1/2005 | Frigstad et al. |
| 2010/0322489 A1* | 12/2010 | Tizhoosh ............ G06K 9/6253 382/128 |
| 2013/0016092 A1* | 1/2013 | Collins ................ A61B 8/469 345/419 |
| 2014/0221832 A1 | 8/2014 | El-Zehiry et al. |
| 2016/0350620 A1 | 12/2016 | Rao et al. |
| 2017/0071671 A1 | 3/2017 | Nuemann et al. |
| 2017/0265846 A1 | 9/2017 | Sui et al. |
| 2018/0055479 A1 | 3/2018 | Lalena |

OTHER PUBLICATIONS

Hsu, Stephen J., et al. "Real-time RNN-based acoustic thermometry with feedback control." AIP Conference Proceedings. vol. 1821. No. 1. AIP Publishing, 2017.

Krizhevsky, Alex, Ilya Sutskever, and Geoffrey E. Hinton. "ImageNet classification with deep convolutional neural networks." Advances in neural information processing systems. 2012.

Smistad, Erik, and Lasse Løvstakken. "Vessel detection in ultrasound images using deep convolutional neural networks." International Workshop on Large-Scale Annotation of Biomedical Data and Expert Label Synthesis. Springer International Publishing, 2016.

U.S. Appl. No. 15/461,563, filed Mar. 17, 2017.

U.S. Appl. No. 15/499,934, filed Apr. 28, 2017.

U.S. Appl. No. 15/691,855, filed Aug. 31, 2017.

* cited by examiner

MACHINE-AIDED WORKFLOW IN ULTRASOUND IMAGING

BACKGROUND

The present embodiments relate to ultrasound imaging. Machine learning has made tremendous progress on addressing image classification and segmentation. For example, a deep convolutional neural network may achieve reasonable performance on hard visual recognition tasks in ultrasound, matching or exceeding human performance in some domains. The classification or segmentation from ultrasound images is used to provide more information to physicians for diagnosis, prognoses, or treatment.

The automated classification or segmentation may assist a sonographer, reducing some time used to examine a patient. An increasing and aging patient population is creating a demand for improved healthcare efficiency. This has led to tremendous need for ultrasound imaging workflow improvement from the standpoint of increased patient throughput, reducing exam times, and reducing user stress through repetitive motion. While standardization of ultrasound examinations and automated segmentation may help, more efficiencies may be found to reduce examination time and resulting user stress.

SUMMARY

By way of introduction, the preferred embodiments described below include methods, instructions, and systems for machine-aided workflow assistance for an ultrasound scanner. Using computer-assisted classification and/or computer-assisted segmentation with or without monitoring the field of view for change, the workflow for ultrasound imaging may be made more efficient. The classification and/or segmentation is used to perform a next act in the sequence of acts making up the ultrasound examination. Rather than requiring a user to determine the act and implement the act, the ultrasound scanner determines and implements the act based on the identification and/or location of an imaged object. For example, the identification of the object as a kidney using a machine-learnt classifier triggers a color flow scan, and the location of the object determines a placement for the color flow region of interest (ROI), avoiding the user having to perform the ROI initiation and/or placement and increasing workflow efficiency.

In a first aspect, a method is provided for machine-aided workflow assistance for an ultrasound scanner. An internal region of a patient is scanned with an ultrasound transducer of the ultrasound scanner. The scanning repeats in an on-going ultrasound examination. A machine-learnt classifier applied to scan data from the scanning during the on-going ultrasound examination identifies an object in the internal region. A machine-learnt segmentor is selected based on the identification of the object. The selection occurs during the on-going ultrasound examination. The selected machine-learnt segmentor segments the object in the scan data during the on-going ultrasound examination. The ultrasound scanner implements a next act in the workflow based on the segmentation of the object. The next act is implemented during the on-going ultrasound examination and without user input to the ultrasound scanner between the segmenting and the implementing. The ultrasound scanner generates an image of the object.

In a second aspect, a system is provided for machine-aided workflow assistance in ultrasound imaging. An ultrasound scanner is configured to scan, with a transducer, a region of a patient with ultrasound. The scan repeats during an examination of the patient. An image processor is configured to apply computer-aided classification of one or more objects of the region from scan data of the scan, to apply computer-aided segmentation of the one or more objects based on the classification, and to alter operation of the ultrasound scanner based on the segmentation of the one or more objects. The alteration of the operation is a next step in a workflow for the examination of the patient. A display is operable to display an image of the region with a graphic showing the alteration and/or the next step in the workflow.

In a third aspect, a method is provided for machine-aided workflow assistance for an ultrasound scanner. The ultrasound scanner scans a patient as part of a workflow for ultrasonically examining the patient. The workflow includes a sequence of acts. The ultrasound scanner monitors a change in a field of view of the scanning. In response to the change, an object is detected from the scanning with a machine-learnt network. The detection includes identifying the object and/or locating the object. Without user control, operation of the ultrasound scanner is altered to increment along the sequence of the workflow. The alteration is based on the identification and/or location of the object.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Image recognition is applied, not just to recognize, but to aid and improve ultrasound imaging workflow. Machine learning-based techniques have been increasingly successful in image classification and segmentation. Simultaneously, the demand for improved patient throughput has increased. Image recognition is used to improve and aid ultrasound imaging workflow for increased patient throughput and efficiency.

In one embodiment, machine learning-based image classification and segmentation techniques are utilized to aid and improve ultrasound imaging workflow. Deviations from standard workflow are suggested and/or implemented based on pathology identification. The image classification and segmentation happens during live scanning to provide real time workflow assistance during the actual live exam, as opposed to providing classification after the fact. The real-time operation allows automatic loading of presets, measurements, and annotations by the ultrasound scanner as opposed to manually entered by the user. Automated workflow modification based on pathology detection is implemented, and the ultrasound scanner clearly communicates to the user when making any workflow modification.

Figure 1:
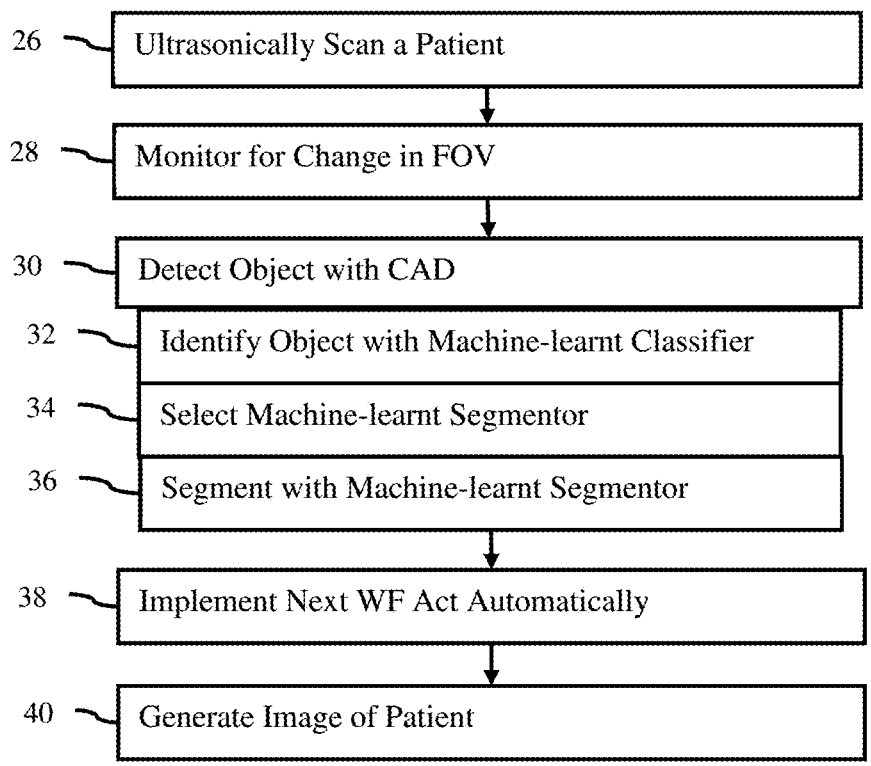
FIG. 1 is a flow chart diagram of one embodiment of a method for machine-aided workflow assistance for an ultrasound scanner.

FIG. 1 shows a method for machine-aided workflow assistance for an ultrasound scanner. During an ultrasound examination of a patient, a sequence of acts is performed. At least some of the acts are performed in response to classification and/or segmentation of an object or objects in an internal region of the patient. The ultrasound scanner automatically performs the acts in response to computer-assisted classification and/or segmentation, allowing the user to avoid altering the ultrasound scanner to implement the acts.

Figure 2:
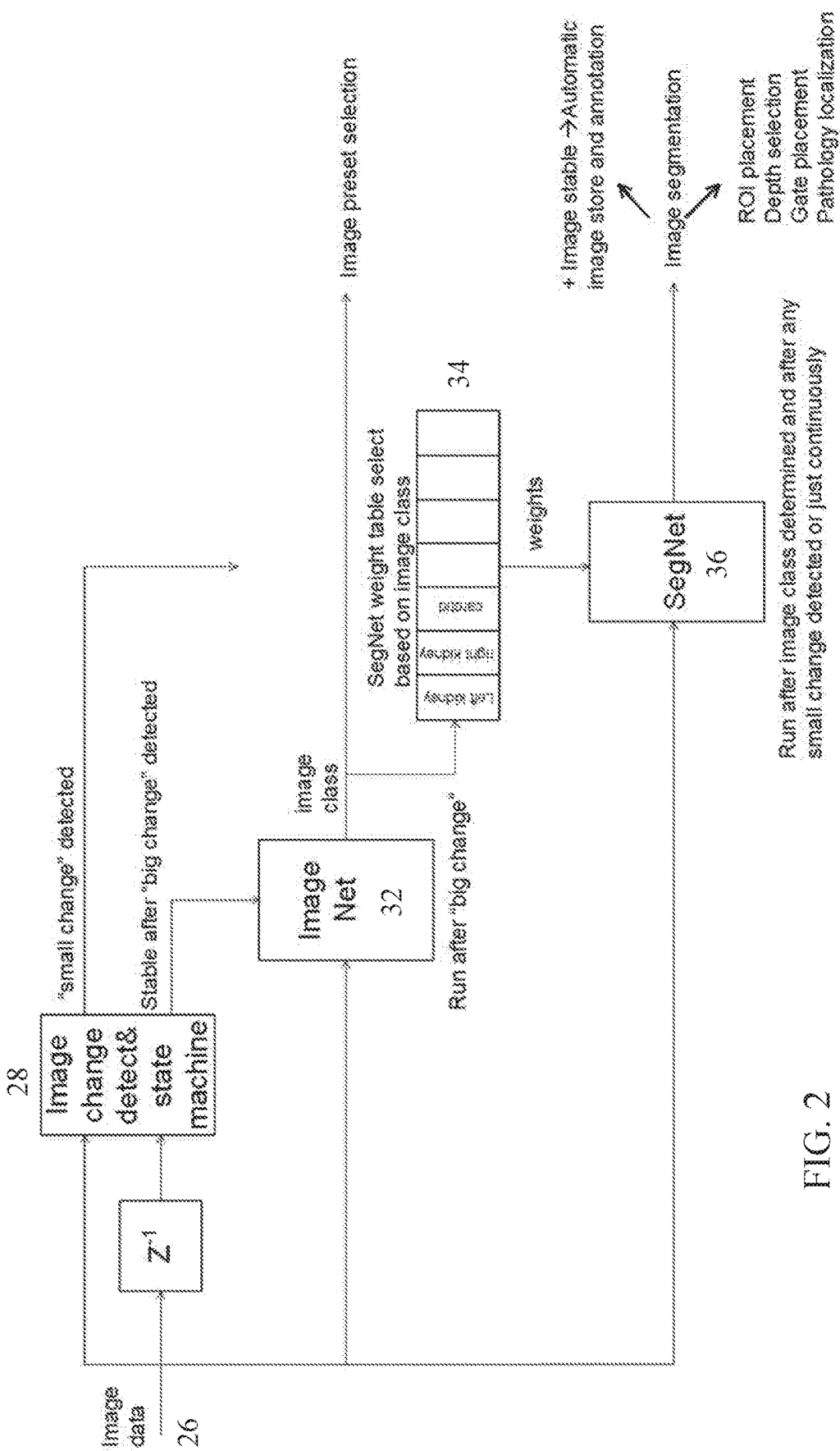
FIG. 2 is a flow chart diagram of another embodiment of a method for machine-aided workflow assistance for an ultrasound scanner.

FIG. 2 shows another embodiment of the method of FIG. 1. The segmentation may be repeated for a steady field of view relative to the patient. When the field of view changes significantly, one or more classifiers are applied to identify the object in the field of view and select an appropriate segmentation. The acts of the workflow relying on the identification and/or segmentation of the object are performed in response to the identification and/or segmentation without user control.

Figure 6:
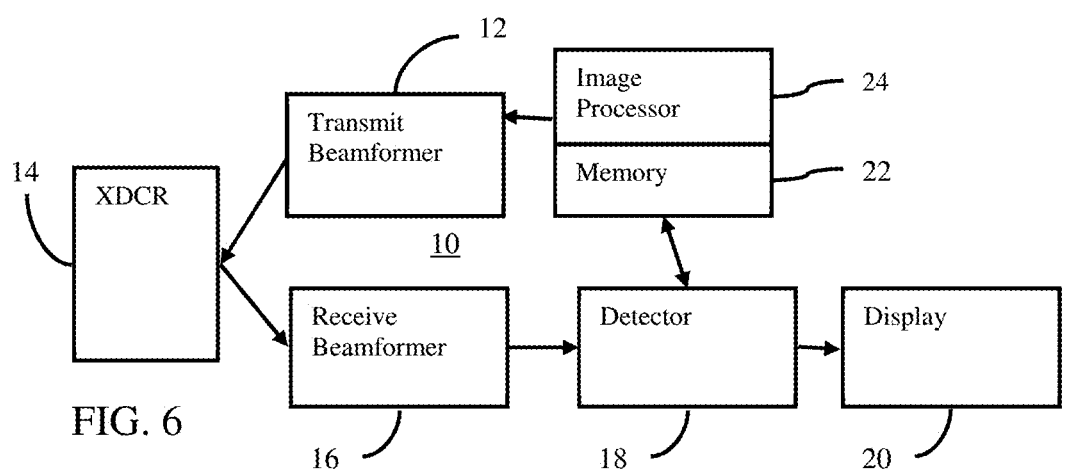
FIG. 6 is one embodiment of a system for machine-aided workflow assistance for ultrasound imaging.

The method is implemented by the system of FIG. 6 or a different system. For example, an ultrasound imaging system generates ultrasound images using beamformers and a transducer. An image processor of the ultrasound imaging system applies computer-assisted detection to identify and/or segment an object and implements acts in the examination workflow in response to the identification and/or segmentation. Beamformers, memory, detectors, and/or other devices may be used to acquire the data, perform one or more of the acts, and/or output the data. The image processor may control the devices to perform the methods of FIGS. 1 and/or 2.

Additional, different, or fewer acts may be provided. For example, the method is performed without generating an image in act 40. As another example, the computer-assisted detection is performed in act 30 without the specific acts 32-36. In yet another example, act 28 is not provided, such as where classification and/or segmentation are performed regardless of any change in the field of view. In other examples, act 32 is provided without acts 34 and 36 or vice versa.

The acts are performed in the order described or shown (e.g., top to bottom or numerical), but may be performed in other orders. For example, segmentation of act 36 is performed prior to identification by classification of act 32. As another example, the monitoring for change of act 28 may be performed after act 32.

In act 26, the ultrasound scanner scans an internal region of a patient with an ultrasound transducer. The ultrasound scanner generates ultrasound images of the patient. The images are generated by scanning the patient.

Any type of ultrasound scanning and corresponding images may be generated, such as B-mode, flow or color mode (e.g., Doppler velocity or power), contrast agent, harmonic, pulsed wave Doppler (i.e., spectral Doppler), M-mode, Doppler tissue (i.e., tissue motion), or other ultrasound imaging mode representing acoustic interaction with the patient. The different modes detect different types of information, such as intensity of acoustic return (e.g., B-mode and M-mode) or velocity (e.g., flow mode or Doppler tissue).

The scan samples a field of view. Electronic steering, the position of the transducer relative to the patient, and/or the structure of the transducer defines a field of view being scanned. The field of view is a point, line, area, or volume internal to the patient. The depth of the field of view (i.e., distance from the transducer for the field of view) is set by the beamformer.

Any anatomy, inserted objects, or abnormalities may be in the field of view. For example, the sonographer is performing an ultrasound examination for a particular organ (e.g., kidney or heart). Other objects include inserted devices (e.g., catheters or stents). Abnormalities are tissue or flow patterns not typical for the organ or patient, such as a lesion, cyst, or regurgitant flow.

The scanning is repeated to continue imaging the patient over an examination period, such as over a five to twenty-minute examination. The transducer and corresponding field of view is moved to locate the object of interest in a survey mode. Once the organ is located, the scanning continues. The type of scanning may change, depending on what is found in the region or due to examining different objects at different times. The workflow for the examination may call for different types of scanning or the same scanning for performing other acts, such as measurements. The repetition is continuous, such as scanning the field of view five, ten, twenty or more times a second. Pauses in scanning during the on-going ultrasound examination of the patient during a single visit or appointment may occur while the sonographer performs an act in the workflow.

During an on-going ultrasound examination, the workflow may include various steps. A decision tree or sequence of steps with or without branching decisions guides the ultrasound examination. Each act is typically implemented by the sonographer. The sonographer controls the ultrasound scanner to cause the step to happen, such as manual tracing a boundary for segmentation, positioning a box on a displayed image for ROI placement, annotating an image, selecting a measurement, indicating measurement locations, initiating measurement, initiating image storage, selecting a patient medical record, and/or naming the image. Any given step may be automated, such as segmenting an image. This automation may speed the workflow. Further automation is provided by triggering and implementing, at least part of, a next step in the workflow based on automatic implementation of the current step. Segmentation and/or classification are used to trigger and implement, at least partly, one or more other steps in the workflow.

The workflow may be unique to the sonographer, a guideline of the hospital or medical practice, a guideline of a professional organization, or other arrangement of acts to be performed for a given type of ultrasound examination. Any level of detail may be provided in the workflow. The workflow sequence addresses the acts to be performed from the start of the examination, such as initially starting with selecting an appropriate transducer for the prescribed examination, to the end of the examination, such as storing or transmitting results.

Figure 3:
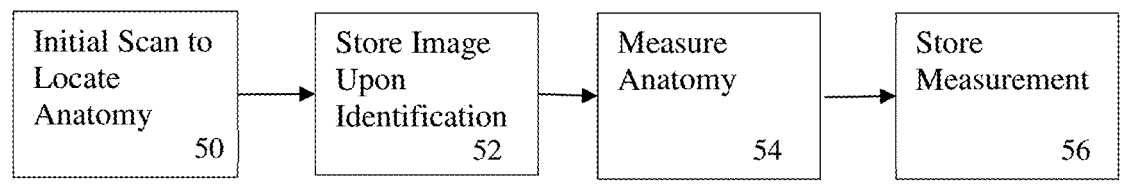
FIG. 3 illustrates an example basic workflow for ultrasound examination.

FIG. 3 shows an example basic workflow for an abdominal ultrasound examination. In step 50, an initial scan is performed to locate the anatomy of interest (e.g., kidney, bladder, or liver). Upon locating the anatomy, a representative image is stored in step 52. The anatomy is then measured in step 54. The measurement may include placing a region of interest (ROI) and measuring with a different type of ultrasound scan (e.g., color flow) or placing calipers to measure a size (e.g., length, area, or volume). In step 56, the measurement is stored. Other workflows include other acts or more detailed steps to be performed. Example workflow steps include configuring the ultrasound scanner to store an image, to review images, to make a measurement, to update a patient record, to annotate an image, to change scan parameters (e.g., transmit frequency, receive frequency, depth of field of view, and/or type of scanning), to change scanning presets or application (e.g., switch from liver scanning to lesion scanning), to place a Doppler gate, to localize pathology, to annotate an image, and/or to transmit results. These various steps provide or lead to providing information to be used for diagnosis, prognosis, and/or treatment, but the various steps take time for a sonographer to implement. Rather than merely automate the known steps, real-time automatic implementation is performed based on the classification and/or segmentation.

Each scan of a plane or volume provides a frame of scan data. An image may be generated from each frame. The scan data is imaging data. An image may be scan data that may be used for imaging, data formatted for display, and/or a displayed image. With persistence or other compounding, images may be generated from multiple frames. Tens, hundreds, or thousands of frames and/or images are created for examining the patient in one examination (e.g., during a given visit of a patient to the sonographer).

The scanning of act 26 continues or is repeated while act 30 is performed. For example, the scanning continues with the identifying of act 32, selecting of act 34, segmenting of act 36, and implementing of act 38. During the live scan, the object detection is performed in real-time. To assist with workflow, the detection occurs in real-time with the continuous scanning. The detection of act 30 in real-time with the scanning of act 26 provides for solutions for workflow enhancement during live scan or during a given ultrasound examination of a patient.

In act 28, the ultrasound scanner monitors for a change in a field of view of the scanning. Due to transducer and/or patient movement, the field of view of the transducer may shift from one region to another region of the patient. The motion is intentional, such as to survey the patient, or unintentional, such as due to sonographer strain or patient shifting.

Once a region or object is found, the transducer may be held in position relative to the patient to continue to scan the region or object for more detailed examination and/or to perform steps of the workflow. While the field of view is maintained at the region or object, some acts may not need to be repeated. For example, the identification of the object from act 32 is not repeated. After some examination, the field of view may be shifted. The shift may lead to needing to repeat the identification of act 32 as a different object may be in the field of view. For example, FIG. 2 shows a branching of the method depending on the amount of change in the field of view where act 32 is performed for big change and acts 32 and 34 are skipped for small or no change. The amount of change is detected in act 28. This amount is compared to a threshold to distinguish between a larger change (e.g., change in the field of view) and smaller changes (e.g., change due to physiological or incidental sonographer or patient motion). For initiating the method, act 32 is performed after completing a survey of the patient to find the object or during the survey to indicate success in finding the object.

Any monitoring of the level of change in the field of view may be used. For example, a correlation (e.g., cross-correlation or minimum sum of absolute differences) between most recently acquired, temporally adjacent frames of scan data is performed. As another example, the correlation is between a template or reference frame of scan data and a most recently acquired frame of scan data. Other measures of the level of change may be used, such as tracking transducer motion with a magnetic or other position sensor.

The amount or level of change is compared to a threshold. Small change occurs when the level of change is below the threshold. Big change occurs when the level of change is above the threshold. For change at the threshold level, the change may be treated as big or small. The ultrasound scanner uses the threshold to identify the level of change. A pattern of change may be used, such as identifying a big change followed by small change over a period (e.g., 10 seconds) for a stable field of view. This pattern indicates a shift in the field of view to a new region and interest in examining the new region. The pattern is identified from one or more thresholds.

The threshold and/or pattern of change link real-time image movement detection to the detection of act 30. For example, the identifying of act 32, selecting of act 34, and segmenting of act 36 are performed in response to the level of change being above a threshold (i.e., change in field of view with or without subsequent stable positioning), and the segmenting of act 36 without repeating the identifying of act 32 and selecting of act 34 is performed in response to the level of change being below the threshold (i.e., continuing scanning of a previous field of view and corresponding previously identified object or objects).

In act 30, the ultrasound scanner detects an object from the scanning. The detection is a classification (e.g., identification) and/or location (e.g., segmentation) of the object. In one embodiment, both classification and location detection are performed in any order.

The detection is performed in response to a determined change or pattern of change. Alternatively, the detection is performed periodically, continuously, or in response to another trigger. The monitoring of act 28 is or is not performed.

The ultrasound scanner or an image processor applies computer-assisted detection to each, one, a subset, or all the frames or images of the sequence acquired by the scanning. Any now known or later developed computer-assisted detection may be applied. For example, pattern matching is used to determine whether a pattern indicative of an organ, anatomical landmark, inserted device, and/or abnormality (e.g., tumor or cyst) is located in the frame or image. As another example, thresholding, random-walker, or other image processing is applied.

For more rapid detection, a machine-learnt detector or network may be applied. In one embodiment, the machine-learnt detector is a deep learnt neural network. Any machine learning or training may be used. A probabilistic boosting tree, support vector machine, neural network, sparse auto-encoding classifier, Bayesian network, or other now known or later developed machine learning may be used. Any semi-supervised, supervised, or unsupervised learning may be used. Hierarchal or other approaches may be used.

For machine training and application of a machine-learnt network, values for any number of features are extracted from samples of scan data. The values for textures of the tissues represented in the scan data are extracted. The texture of the tissue is represented by the measures of the scan data.

Each feature defines a kernel for convolution with the data. The results of the convolution are a value of the feature. By placing the kernel at different locations, values for that feature at different locations are provided. Given one feature, the values of that feature at different locations are calculated. Features for other texture information than convolution may be used, such as identifying a maximum or minimum. Other features than texture information may be used.

In one embodiment, the features are manually designed. The feature or features to be used are pre-determined based on a programmer's experience or testing. Example features include scaled invariant feature transformation, histogram of oriented gradients, local binary pattern, gray-level co-occurrence matrix, Haar wavelets, steerable, or combinations thereof. Feature extraction computes features from the ultrasound image to better capture information distinguishing one or more organs or regions.

In another embodiment, deep-learnt features are used. The values are extracted from the scan data for features learned from machine learning. Deep machine learning learns features represented in training data as well as training the detector, rather than just training the detector from the manually designated features. The relevant features are automatically determined as part of training. This ability allows for the generic training on arbitrary data (i.e., training data with known outcomes) that may internally determine features, such as textures. By training the network with labeled outcomes (i.e., ground truth for the detection (e.g., identity or location of the object)), the network learns what features are relevant or may be ignored for detection.

Any deep learning approach or architecture may be used. For example, a convolutional neural network is used. The network may include convolutional, sub-sampling (e.g., max pooling), fully connected layers, and/or other types of layers. By using convolution, the number of possible features to be tested is limited. The fully connected layers operate to fully connect the features as limited by the convolution layer after maximum pooling. Other features may be added to the fully connected layers, such as non-imaging or clinical information. Any combination of layers may be provided.

The machine-learnt network, with or without deep learning, is trained to associate the categorical labels (output identity and/or segmentation) to the extracted values of one or more features. The machine-learning uses training data with ground truth, such as values for features extracted from frames of data for patients with known objects and/or segmentations, to learn to detect based on the input feature vector. The resulting machine-learnt network is a matrix for inputs, weighting, and combination to output the detection. Using the matrix or matrices, the image processor inputs the extracted values for features and outputs the detection.

Additional information than scan data may be used for detecting. For example, values of clinical measurements for the patient are used. The detector is trained to detect based on the extracted values for the features in the scan data as well as the additional measurements. Genetic data, blood-based diagnostics, family history, sex, weight, and/or other information are input as a feature.

Where the computer-assisted detection is based on machine learning, self-learning or feedback learning may be used. Once a physician reviews detected objects and indicates whether the detection is correct, the indication and sample may be later used as training data. This information may be used as further training data to re-learn or update the detector with additional ground truth.

Different computer-assisted detectors may detect different types of objects and/or objects in different situations. Multiple detectors may be applied to each frame. In one embodiment, the detectors to be applied are selected based on the type of examination. For example, the user configures the ultrasound scanner for a breast examination. A detector or detectors for detecting suspicious objects (e.g., tumors and/or cysts) in the breast, for detecting specific breast anatomy or landmarks, and/or for detecting the breast are selected and applied. As another example, the user configures the ultrasound scanner for breast examination to detect cancer. A detector or detectors for detecting cancer objects in the breast are selected. The selection is automatic by the processor, or the user selects the detectors. In another embodiment, the detector detects different anatomy so that detection occurs for scanning any region of the patient. A hierarchy of binary detectors and/or one detector to detect different objects is applied.

The detector classifies (e.g., identifies) and/or segments one or more objects. For example, a machine-learnt classifier or classifiers identify one or more objects represented in the scan data. The classifier classifies the organ or region of the patient from the extracted values of the features. The values are input to the machine-learnt classifier implemented by the image processor. By applying the classifier, the organ or other objects represented in the scan data are classified. As another example, a machine-learnt segmentor or segmentors locate one or more objects represented in the scan data. The segmentor determines a location, such as all tissue belonging to an organ, a boundary, and/or a center, from the extracted values of the features. The values are input to the machine-learnt segmentor implemented by the image processor. Different machine-learnt detectors or networks are provided for classification and segmentation. Alternatively, one detector is trained to both classify and segment.

The computer-assisted detection is applied during the acquisition of the frames or images (i.e., during the scanning and/or ultrasound examination). The application is in real-time. The period to process a frame is equal to or less than the period to acquire a limited number of new frames, such as only one, two, five, or ten frames. The real-time application allows the application to occur within a second or two of creating the scan. Machine-learnt detectors may operate more quickly than template matching or other detection.

Acts 32, 34, and 36 show one example detection of act 30. FIG. 2 shows a further process flow for these three example detection acts. In act 32, the object is identified with a machine-learnt or other computer-assisted classifier, then a machine-learnt segmentor is selected in act 34 based on the identification, and then the identified object is segmented with the selected machine-learnt or other computer-assisted segmentor. In other embodiments, only act 32, only act 36, or acts 32 and 36 without act 34 are performed.

In act 32, the ultrasound scanner or image processor identifies one or more objects in the internal region of the patient. By applying a machine-learnt classifier to the scan data (i.e., inputting values for a feature vector derived from the scan data), the object or objects are identified. In one embodiment, a classifier based on ImageNet is used to identify.

One or more objects are identified in any number of the frames or images. Where the computer-aided characterization runs in real-time with the scanning, the object or objects are identified during the scanning. The machine-learnt classifier may be trained to classify for multiple objects in a region. Alternatively, the machine-learnt classifier may be trained to identify one particular object. More than one machine-learnt classifier may be applied to identify multiple objects. The machine-learnt classifier or classifiers are chosen based on the imaging application or presets used to scan, such as applying a classifier of whether an object is a liver or not based on performing a liver scan.

The identification is of the object. A label identifying the object is determined. For example, a type of organ or anatomical landmark is determined (e.g., kidney or carotid artery, or apex of a left ventricle). As another example, a catheter is identified as a catheter. In yet another example, an abnormality is identified. The abnormality may be identified as an abnormality or more specifically (e.g., cyst, tumor, or cancer).

In act 34, the ultrasound scanner or image processor selects a machine-learnt segmentor. The machine-learnt segmentor is trained to a specific type or particular object, such as a kidney segmentor. Alternatively, the segmentor is trained to segment more than one type of object.

The selection is based on the identification of the object. The classifier determines that the field of view includes one or more particular objects. A corresponding segmentor or segmentors are selected for segmenting the object or objects. For example, a machine-learnt segmentor of a catheter, organ, or anatomical landmark is selected.

The selection occurs during the on-going ultrasound examination. The classification is performed while the patient is being scanned. Similarly, the selection occurs within a fraction of a second after the classification and while the patient is being scanned. Less rapid selection may occur, such as within a few seconds while other classification is performed for other objects.

The selection of the machine-learnt segmentor is selection of a matrix or matrices. Each segmentor may use a different network architecture. A bank of segmentors trained for different objects is available, and one or a sub-set is selected based on the classification. Alternatively, a same or similar architecture is used for different segmentors and/or classifiers. Different segmentors and/or classifiers have different weights. The selection is of weights for the nodes of the network. In one embodiment, one network is well trained for segmenting the heart and another network is well trained for segmenting one or more organs in the abdomen (i.e. liver, spleen, kidney). By selecting which weights to deploy to the network or trained network, the appropriate network is applied for segmentation.

In act 36, the ultrasound scanner or image processor segments the object in the scan data. The selected machine-learnt segmentor is applied. In one embodiment, a machine-learnt segmentor based on SegNet is used. Values for features are extracted and input to the machine-learnt segmentor. Where deep learning is used, the segmentor extracts the values for the features.

The segmentor is applied during the on-going ultrasound examination. Within a fraction of a second or a few seconds from selection of the segmentor, the segmentor is applied and outputs the location information. While acquiring a next frame of scan data or within the time to acquire ten or twenty frames, the segmentor is applied. More or less rapid application may be provided.

The segmentor may continue to be applied. As each new frame of data is acquired by repeating the scanning, the segmentor is applied. Location information is provided for each frame. This continues until there is a large change or pattern of change in the field of view. Once the field of view stabilizes, the same or different segmentor is applied to each frame of scan data. In alternative embodiments, the segmentor is applied to every other or another subset of the frames acquired in the on-going examination.

The machine-learnt segmentor indicates a location of the object. The classifier identifies the object in the field of view, and the segmentor determines the location of the object in the field of view. The location is a boundary, binary mask (i.e., every pixel, voxel, or sample point belonging to the object), center, spatial extent (e.g., fit approximate or model shape), or other representation of spatial position, orientation, and/or scale. The machine-learnt segmentor determines the location of the object based on the input values for the feature vector, such values extracted from the scan data for the frame or frames.

In act 38, the ultrasound scanner or image processor implements a next act in the workflow based on the segmentation and/or classification of the object. The implementation is without user input between the detection, classification, and/or segmentation and the implementation. The operation of the ultrasound scanner is altered to increment along the sequence of the workflow without user control of the alteration. The user or image processor may select the workflow, such as selecting based on classification. During incrementation to at least one of the steps of the workflow, the ultrasound scanner performs all or part of the step without user entry of activation or other information to perform that part. For example, a ROI or measurement designator is placed on an image and ROI scanning or measurement performed after segmentation without the user having to place the ROI or measurement designator and/or without the user having to activate the ROI scanning or measurement. Once anatomy has been successfully identified and/or segmented, the identity or location information is utilized to improve the imaging workflow for the user by avoiding at least one user interaction with the ultrasound scanner. This allows the user to continue to focus on scanning, visual interpretation of the results of the scanning, and monitoring the examination.

Any number of steps of the workflow may be triggered by and/or use the identity and/or location information. Any given step that has sufficient information to be triggered and/or performed occurs without user input. The next act or acts of the workflow are implemented during the on-going ultrasound examination. An action to be taken in a sequence of actions of the on-going ultrasound examination is implemented automatically.

The alteration in operation of the ultrasound scanner to implement the step or action in the workflow is based on the identification and/or location of the object. The next act may be more focused scanning on the object, so uses both identification and location. The ultrasound scanner is configured to scan the object. For example, a Doppler gate is positioned based on the identification and location (e.g., position in a regurgitant flow region of the heart). The gate is automatically positioned in a vessel upon entry into a Doppler or spectral mode of imaging, and/or the gate is positioned and the Doppler or spectral mode of imaging is initiated without the user having to position and/or initiate. As another example, the imaging or scanning presets are altered. The user may have initially selected a preset configuring the ultrasound scanner to scan, such as selecting liver imaging. The identification and/or location may be used to select a more refined set of presets appropriate for the identified object and/or location, such as selecting presets for imaging a liver having a particular shape and/or position relative to other organs. As another example, the user may have selected a preset for cardiac system imaging, and then the image processor alters the presets to be for imaging a particular identified artery, heart chamber, and/or valve. In yet another example, the location information indicates an orientation of a vessel or fluid region. The scanning configuration for flow imaging is altered to steer the beams to be more along a direction of flow and/or to include velocity correction to account of the angle of the scan lines from the transducer to the direction of flow. The user having to perform these acts during the scanning may be avoided due to identification and/or location determination and automated incrementation of the workflow.

The next act may be to store an image or frame of scan data. For example, identification is used to trigger storage of a representative image of the object of interest. As another example, locating the object after identification may be used to trigger storage of an image of the object annotated with segmentation, identification, and/or measurement information. The previously input patient information is used to automatically store the image or images in the medical record of the patient. The automated image storage occurs without the user having to trigger and/or input other information, saving the user time and effort.

Figure 4:
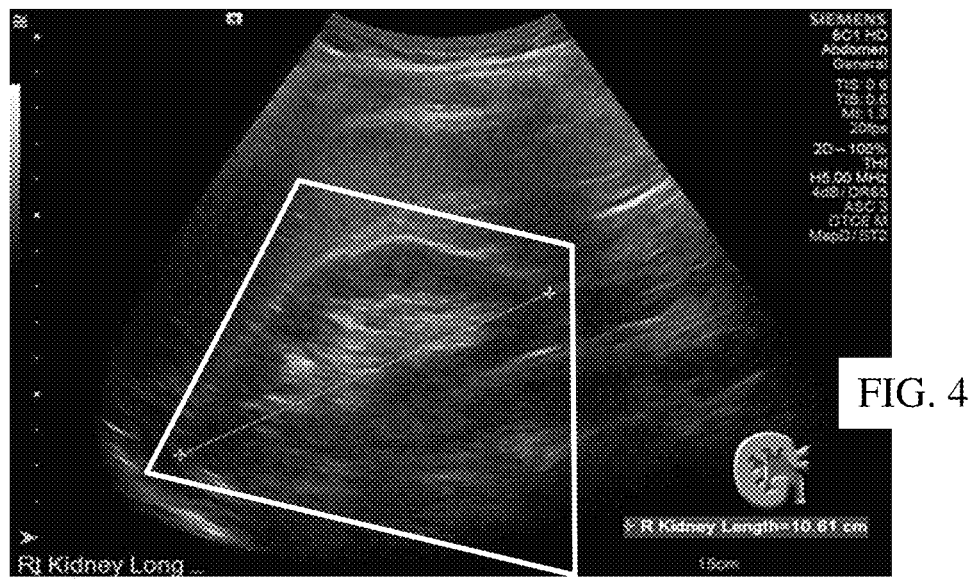
FIG. 4 illustrates an example ultrasound image with a region of interest designator placed as a next act in a workflow.
Figure 5:
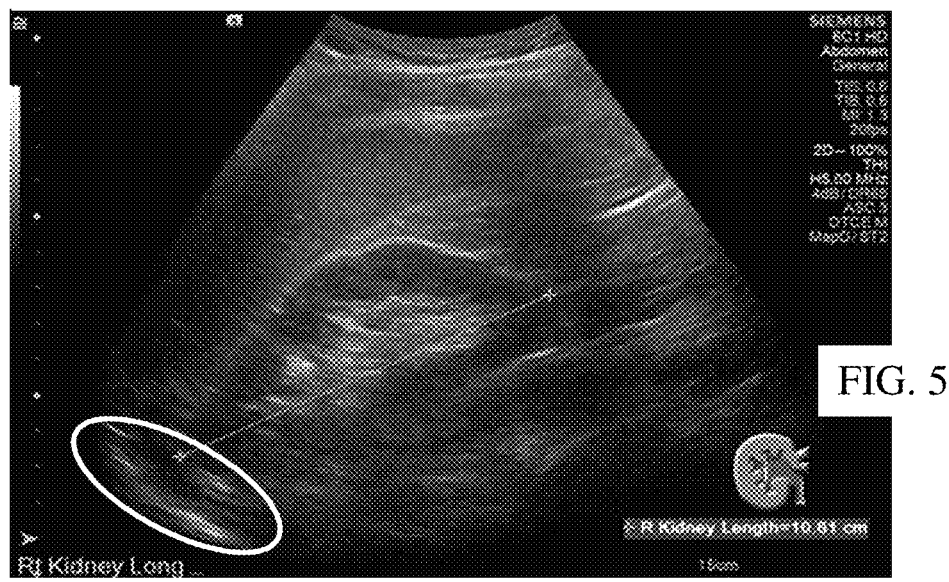
FIG. 5 illustrates an example ultrasound image with a measurement caliper designator placed as a next act in a workflow.

The next act may be measurement. Based on the identification of the object, the relevant measurement or measurements are loaded or implemented. By pre-loading, the user having to select which measurements to perform may be avoided. By implementation, the user having to activate may be avoided. Rather than the user having to place calipers or trace a boundary and/or having to activate the measurement, the ultrasound scanner uses the segmentation to place calipers at given landmarks or as the trace and activates the measurement. FIGS. 4 and 5 shows an example where the kidney is identified and a maximum length measurement is automatically performed based on the segmentation of the identified kidney. FIGS. 4 and 5 show indication of the measurement as automated placement of the calipers and a line between the calipers. The measurement of the identified object is performed based on the identification and/or location without user control of the measurement step in the workflow.

The next act may be annotation of an image. Any annotation may be included in a workflow, such as labeling the image with identification of the anatomy, showing segmentation (e.g., highlighting the object in color or different objects in different colors, extracting the object, or showing a boundary trace), and/or indicating a value of a measurement. The annotation is alphanumeric text and/or another graphic. The annotation is added to a displayed image based on the identification and/or location without the user having to add the annotation. The annotation may be positioned based on the location of the object.

The next act may be identification of a vessel or fluid region boundary and/or color flow scanning. The location information provides the boundary, allowing for color flow scanning with flow information being shown for locations within the boundary and B-mode being shown for other locations. Rather than the user having to identify and trace the vessel or fluid region and then activate color flow imaging, the ultrasound scanner uses the identification and/or segmentation to establish the flow display containment relative to B-mode locations and activate the flow scanning.

The next act may be placing a ROI. The identification indicates that the object of interest is in the field of view. The location information indicates a position of the object around or in which the ROI is to be placed. For example, the boundary of the object is used. The ROI is placed to cover the boundary with any tolerance beyond the boundary. The position, boundary, and/or size of the object from segmentation is used to locate the ROI. FIG. 4 shows an example of an ROI as a box placed around or encompassing the entire kidney. Rather than the user having to identify the kidney and interact with the user interface to place the ROI, the ultrasound scanner implements the placement of the ROI, such as a color region of interest. The ROI is used for a different type of imaging or scanning, such as color flow. The ROI-based scanning may likewise be started without user initiation given the scanner placed ROI. Color Doppler imaging automatically starts off with an ROI positioned at anatomy of interest.

Continuous real-time segmentation may additionally provide tracking information to allow the ROI position to be updated as the probe or patient moves. The ROI or other location (e.g., Doppler gate position) is maintained on the anatomical landmarks based on repeating the segmentation for subsequent frames of scan data.

The next act may be altering a depth of the scanning. The frequency of the transmit waveform may also be altered with depth. Higher frequencies attenuate more rapidly but provide greater resolution. By matching the frequency to the depth, more optimized scanning is provided. The identification of an object (e.g., diaphragm) and location of that object may be used to establish the depth. The depth of the field of view is altered as a step in the workflow to refine the examination. FIG. 5 shows an example where the ultrasound examination is to study the kidney. The diaphragm (designated generally by the oval) is identified and located. The depth of the scan is reduced to avoid scanning deeper than the diaphragm, resulting in greater detail for imaging the kidney. In other embodiments, the deepest extent of the kidney is used to establish the depth. Rather than the user having to make the depth change, the depth change occurs automatically.

The next act may be associated with identification of an abnormality (i.e., identifying a pathology). For example, the classifier identifies a lesion or tumor during a liver, kidney, or breast examination. The workflow includes a branch of steps to be performed upon detection of the abnormality. The classifier-based detection triggers implementation of the branch of steps. The steps may include placement of an ROI or magnification box (e.g., Res box) around pathology, measurements to measure the pathology (e.g., size, shape, flow, and/or elasticity), annotation of the pathology, storage of an image showing the pathology, or other steps. The ultrasound scanner performs one or more of the steps based on the identification and/or location of the pathology without the user having to control the steps.

Parts of steps may be automated, such as showing a list of measurements that could be performed on the user interface for selection by the user. The user does not have to activate the display of the list. The pattern of change may be used, such as implementing measurement, annotation, and image store in sequence without user input once the field of view is stable at the pathology or object. Other orders of steps may be provided, such as automatic advancement of quantification workflow to next task based on completion of image storage.

In act 40 of FIG. 1, the ultrasound scanner or image processor generates an image of the object. The imaging may correspond to the scanning, such that each acquired frame of scan data is used to generate an image. Images may be generated for only one or fewer than all frames from the scanning.

The generated image may be responsive to the performance or start of performance of a next act to be implemented automatically. Since the user is not implementing the step on the workflow, a visual indication that the ultrasound scanner is implementing the act is provided to the user. For example, an annotation, measurement position, measurement result, or ROI is included in the image. As another example, a confirmation of image storage or saving to a patient's medical record is included. In yet another example, values for settings (e.g., preset values, depth of field of view, or scan settings) are displayed. A notification of a change without specifics may be provided on the image or user interface.

The performance of the next step in the workflow is shown by text or other graphic. A line, box, or other graphic indicates performance or results of performance of the one or more steps in the workflow. A graphic representing the work flow with the current step highlighted and/or completed steps distinguished from uncompleted steps may be displayed.

The identification and/or location information may be included on the image. For example, color tinting is added. Different objects are tinted differently or a given object is tinted where others are not. A marker, line, box, or other graphics may be used to show segmentation. Annotation for identification may be used.

Due to automation of the workflow based on the classification and segmentation, one or more steps in the workflow may be more rapidly performed. Delay for user entry or configuration of the ultrasound scanner is reduced or avoided. The user may confirm proper placement, measurement or other information as part of the step, but user initial placement or entry for measurement may be avoided. A greater throughput per sonographer may result.

FIG. 6 shows one embodiment of a system for machine-aided workflow assistance in ultrasound imaging. The system is an ultrasound scanner 10, which applies computer-assisted or machine-learnt classification and segmentation. The ultrasound scanner 10 is configured by the machine-learnt detectors to identify an object and/or segment an object. Steps of a workflow for ultrasound examination are implemented automatically based on the classification and/or segmentation. The classification, segmentation, and workflow implementation occur in real-time with scanning and/or during an ultrasound examination.

The ultrasound scanner 10 is a medical diagnostic ultrasound imaging system. The ultrasound scanner 10 is configured to scan, with the transducer 14, a region of a patient with ultrasound. The scanning repeats during an examination of the patient. In alternative embodiments, the ultrasound scanner 10 includes a personal computer, workstation, PACS station, or other arrangement at a same location or distributed over a network for real-time imaging from scan data acquired from the patient through connection with beamformers 12, 16 and transducer 14.

The ultrasound scanner 10 implements the method of FIG. 1, the method of FIG. 2, or other methods. The ultrasound scanner 10 includes a transmit beamformer 12, a transducer 14, a receive beamformer 16, a detector 18, a display 20, a memory 22, and an image processor 24. Additional, different or fewer components may be provided. For example, a user input is provided for adjustment of automated placement and/or for configuring the ultrasound system 10 for user controlled workflow steps.

The transmit beamformer 12 is an ultrasound transmitter, memory, pulser, analog circuit, digital circuit, or combinations thereof. The transmit beamformer 12 is configured to generate waveforms for a plurality of channels with different or relative amplitudes, delays, and/or phasing. The waveforms are generated and applied to a transducer array with any timing or pulse repetition frequency. For example, the transmit beamformer 12 generates a sequence of pulses for B-mode scanning in a linear, sector, or Vector® format. As another example, the transmit beamformer 12 generates a sequence of pulses for color flow scanning, such as pulses for forming 2-12 beams in an ongoing flow sample count per scan line for a ROI within a B-mode field of view. In yet another example, the transmit beamformer 12 generates pulses for elasticity or shear imaging. The transmit beamformer 12 may generate a beam for acoustic radiation force impulse. The intensity of the beam causes a shear wave or longitudinal wave to be generated from the focal point. The transmit beamformer 12 then generates beams for tracking the tissue response to the generated wave.

The transmit beamformer 12 connects with the transducer 14, such as through a transmit/receive switch. Upon transmission of acoustic waves from the transducer 14 in response to the generated waves, one or more beams are formed during a given transmit event. The beams are for B-mode, color flow mode, elasticity, shear wave, and/or other modes of imaging. A sequence of transmit beams are generated to scan a one, two or three-dimensional region. Sector, Vector®, linear, or other scan formats may be used.

The transducer 14 is a 1-, 1.25-, 1.5-, 1.75- or 2-dimensional array of piezoelectric or capacitive membrane elements. The transducer 14 includes a plurality of elements for transducing between acoustic and electrical energies. For example, the transducer 14 is a one-dimensional PZT array with about 64-256 elements.

The transducer 14 connects with the transmit beamformer 12 for converting electrical waveforms into acoustic waveforms, and connects with the receive beamformer 16 for converting acoustic echoes into electrical signals. For scanning with ultrasound, the transducer 14 transmits acoustic energy and receives echoes. The receive signals are generated in response to ultrasound energy (echoes) impinging on the elements of the transducer 14.

The receive beamformer 16 includes a plurality of channels with amplifiers, delays, and/or phase rotators, and one or more summers. Each channel connects with one or more transducer elements. The receive beamformer 16 applies relative delays, phases, and/or apodization to form one or more receive beams in response to each transmission for imaging. Dynamic focusing on receive may be provided. Relative delays and/or phasing and summation of signals from different elements provide beamformation. The receive beamformer 16 outputs data representing spatial locations using the received acoustic signals. In alternative embodiments, the receive beamformer 16 is a processor for generating samples using Fourier or other transforms.

The receive beamformer 16 may include a filter, such as a filter for isolating information at a second harmonic, transmit (i.e., fundamental), or other frequency band relative to the transmit frequency band. Such information may more likely include desired tissue, contrast agent, and/or flow information. In another embodiment, the receive beamformer 16 includes a memory or buffer and a filter or adder. Two or more receive beams are combined to isolate information at a desired frequency band, such as a second harmonic, cubic fundamental, or another band.

The receive beamformer 16 outputs beam summed data representing spatial or sample locations. Data for a single location, locations along a line, locations for an area, or locations for a volume are output. The data beamformed in response to a complete scan of a region is a frame of data.

The detector 18 is a B-mode detector, Doppler detector, pulsed wave Doppler detector, correlation processor, Fourier transform processor, filter, other now known or later developed processor for implementing an ultrasound imaging mode, or combinations thereof. The detector 18 provides detection for the imaging modes, such as including a Doppler detector (e.g., estimator) and a B-mode detector.

Other post-beamformation components may be provided. A spatial filter, temporal filter, and/or scan converter may be included. The detector 18 or other components outputs display values, such as detecting, mapping the detected values to display values, and formatting the display values or detected values into a display format.

The image processor 24 is a control processor, general processor, digital signal processor, graphics processing unit, application specific integrated circuit, field programmable gate array, network, server, group of processors, combinations thereof, or other now known or later developed device for detecting objects in images and controlling the ultrasound system 10 to assist in the examination workflow. The image processor 24 is separate from or part of the detector 18. As a separate device, the image processor 24 requests, receives, accesses, or loads data at any stage of processing (e.g., beamformed, detected, scan converted, display mapped or other stage) for detecting and controlling. The image processor 24 is configured by software, firmware, and/or hardware to perform or cause performance of the acts of FIG. 1 or 2.

The image processor 24 is configured to monitor the scan data over time for change in a field of view. Using correlation or other approach, the amount of change or pattern of change is used to determine whether to apply segmentation based on previous object identification or to apply classification and selection of a new segmentor. The image processor 24 is configured to classify by applying computer-aided classification in response to the change being above a threshold or a pattern of change defined by one or more thresholds.

The image processor 24 is configured to apply computer-aided classification of one or more objects of the region from scan data of the scan. For example, a machine-learnt classifier is configured to identify the one or more objects as organs and/or abnormalities. The image processor 24 is configured to apply computer-aided segmentation of the one or more objects based on the classification. A segmentor is selected based on the identification of the object. The segmentor may be a machine-learnt segmentor configured to locate the one or more organs and/or abnormalities.

The image processor 24 is configured to alter operation of the ultrasound scanner based on the classification and/or segmentation of the one or more objects. The alteration is to implement a next step or steps in a workflow for the examination of the patient. The workflow is a sequence of steps in a decision tree from initial scanning to completion of the examination of the patient with ultrasound. Based on the object identification and/or segmentation performed in real-time with the scanning, the next step or steps in the decision tree may be implemented by the ultrasound scanner 10 with no or less user interaction also in real time. For example, the ultrasound scanner places a region of interest, change of depth for the scan, and/or measurement of the one or more objects based on and in response to classification and segmentation.

The image processor 24 or detector 18 generates and outputs images or values to the display 20. For example, B-mode or mixed mode (e.g., B-mode and flow mode) images are output. Text, numerical indication, or graphic may be added and displayed to the user. A graph may be displayed. For example, an annotation marking a detected object, a flag indicating the image as including a detected object, the derived value of a measurement, a ROI, or other object related information is output on the image. The image includes an indication of performance or completion of performance of one or more steps in the workflow. Other indications may be provided, such as a flashing button.

The display 20 is a CRT, LCD, monitor, plasma, projector, printer, or other device for displaying an image or sequence of images. Any now known or later developed display 20 may be used. Each image is of the scan region of the patient. Other information, such as an annotation (e.g., graphic) showing alteration and/or indication of a step in the workflow (e.g., ROI placement indicated by an ROI added to the image), is output on, with, or as part of the image. The display 20 is operable to display one image or a sequence of images. The display 20 displays two-dimensional images or three-dimensional representations.

The detector 18, image processor 24, the receive beamformer 16, and the transmit beamformer 12 operate pursuant to instructions stored in the memory 22 or another memory. The instructions configure the system for performance of the acts of FIG. 1. The instructions configure the detector 18, the image processor 24, the receive beamformer 16, and/or the transmit beamformer 12 for operation by being loaded into a controller, by causing loading of a table of values, and/or by being executed.

The memory 22 is a non-transitory computer readable storage media. The instructions for implementing the processes, methods and/or techniques discussed herein are provided on the computer-readable storage media or memories, such as a cache, buffer, RAM, removable media, hard drive or other computer readable storage media. Computer readable storage media include various types of volatile and nonvolatile storage media. The functions, acts, or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing, and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for machine-aided workflow assistance for an ultrasound scanner, the method comprising:

scanning an internal region of a patient with an ultrasound transducer of the ultrasound scanner, the scanning repeating in an on-going ultrasound examination;

identifying, by a machine-learnt classifier applied to scan data from the scanning during the on-going ultrasound examination, an object in the internal region;

selecting a machine-learnt segmentor based on the identification of the object, the selecting occurring during the on-going ultrasound examination;

segmenting, by the selected machine-learnt segmentor during the on-going ultrasound examination, the object in the scan data;

implementing, by the ultrasound scanner, a next act in the workflow based on the segmentation of the object, the next act implemented during the on-going ultrasound examination and without user input to the ultrasound scanner between the segmenting and the implementing; and generating, by the ultrasound scanner, an image of the object.

2. The method of claim 1 wherein scanning comprises scanning continuously with the identifying, selecting, segmenting and implementing occurring in real-time with the continuous scanning.

3. The method of claim 1 wherein identifying comprises identifying an organ or inserted device in the internal region, and wherein selecting comprises selecting the machine-learnt segmentor trained for the organ or the inserted device.

4. The method of claim 1 wherein identifying comprises identifying an abnormality in the internal region, and wherein implementing comprises implementing the next act based on the abnormality.

5. The method of claim 1 wherein selecting comprises selecting weights configuring the machine-learnt segmentor for the object as identified.

6. The method of claim 1 wherein segmenting comprises locating a boundary of the object, and wherein implementing comprises implementing as a function of the boundary.

7. The method of claim 1 wherein implementing comprises implementing the next act as configuring the ultrasound scanner to scan the object, as storing the image in a medical record of the patient, as establishing a region of interest around or within the object, and/or as arranging for measurement of the object on a user interface of the ultrasound scanner.

8. The method of claim 1 wherein implementing comprises implementing the next act in the workflow as an action taken in a sequence of actions of the on-going ultrasound examination, the action taken being triggered by the segmentation.

9. The method of claim 1 wherein scanning comprises B-mode scanning, and wherein implementing comprises implementing the next act as setting a color region of interest based on the identification of the object, a position of the object from the segmenting, and a size of the object from the segmenting.

10. The method of claim 1 wherein implementing comprises implementing the next act as a change to a scan depth of the scanning based on an identification of the object and a location of the object from the segmentation.

11. The method of claim 1 wherein generating the image comprises generating the image as responsive to performance of the next act.

12. The method of claim 1 wherein generating the image comprises generating the image as showing performance of the next act with a graphic.

13. The method of claim 1 further comprising detecting a level of change between the scan data from different times and performing the identifying, selecting, and segmenting in response to the level of change being above a threshold and performing the segmenting without repeating the identifying and selecting in response to the level of change being below the threshold.

14. A system for machine-aided workflow assistance in ultrasound imaging, the system comprising:

an ultrasound scanner configured to scan, with a transducer, a region of a patient with ultrasound, the scan repeating during an examination of the patient;

an image processor configured to apply computer-aided classification of one or more objects of the region from scan data of the scan, to apply computer-aided segmentation of the one or more objects based on the classification, and to alter operation of the ultrasound scanner based on the segmentation of the one or more objects, the alteration of the operation being a next step in a workflow for the examination of the patient; and a display operable to display an image of the region with a graphic showing the alteration and/or the next step in the workflow.

15. The system of claim 14 wherein the image processor is configured to monitor the scan data over time for change in a field of view and is configured to apply the computer-aided classification in response to the change being above a threshold.

16. The system of claim 14 wherein the computer-aided classification comprises application of a machine-learnt classifier configured to identify the one or more objects as organs and/or abnormalities, and wherein the computer-aided segmentation comprises application of a machine-learnt segmentor configured to locate the one or more organs and/or abnormalities.

17. The system of claim 14 wherein the workflow comprises a sequence of steps in a decision tree from initial scanning to completion of the examination of the patient with ultrasound, the next step comprising one of the steps in the decision tree.

18. The system of claim 14 wherein the alteration comprises placement of a region of interest, change of depth for the scan, and/or measurement of the one or more objects.

19. A method for machine-aided workflow assistance for an ultrasound scanner, the method comprising:

scanning, by the ultrasound scanner, a patient as part of a workflow for ultrasonically examining the patient, the workflow including a sequence of acts;

monitoring, by the ultrasound scanner, a change in a field of view of the scanning;

detecting, in response to the change, an object from the scanning with a machine-learnt network, the detecting comprising identifying the object and/or locating the object, wherein detecting comprises identifying the object with a machine-learnt classifier and then segmenting the identified object with a machine-learnt segmentor selected based on the identification; and altering, without user control, operation of the ultrasound scanner to increment along the sequence of the workflow, the alteration being based on the identification and/or location of the object.

20. The method of claim 19 wherein monitoring comprises identifying the change as above a threshold, and wherein altering comprises storing an image with an annotation of the identification and location, altering a depth of the field of view, placing a region of interest, and/or placing a gate.

* * * * *